US008932275B2

(12) United States Patent
Smith (10) Patent No.: US 8,932,275 B2
(45) Date of Patent: Jan. 13, 2015

(54) SURGICAL SEAL ASSEMBLY (75) Inventor: Robert C. Smith, Middletown, CT (US)

(73) Assignee: Covidien LP, Mansfield, MA (US)

( * ) Notice: Subject to any disclaimer, the term of this patent is extended or adjusted under 35 U.S.C. 154(b) by 1578 days.

(21) Appl. No.: 11/823,560

(22) Filed: Jun. 28, 2007

(65) Prior Publication Data

US 2009/0005740 A1 Jan. 1, 2009

Related U.S. Application Data (60) Provisional application No. 60/819,434, filed on Jul. 7, 2006.

(51) Int. Cl.
| A61M 31/00 | (2006.01) |
| A61M 5/178 | (2006.01) |
| A61M 5/00 | (2006.01) |
| A61M 5/14 | (2006.01) |
| A61M 39/06 | (2006.01) |

(52) U.S. Cl.
CPC ... *A61M 39/0606* (2013.01); *A61M 2039/0626* (2013.01); *A61M 2039/0633* (2013.01); *A61M 2039/0646* (2013.01); *A61M 2039/0653* (2013.01); *A61M 2039/0686* (2013.01)
USPC . 604/513; 604/506; 604/167.01; 604/167.03; 604/167.04; 604/167.06; 604/256

(58) Field of Classification Search
USPC .......... 604/246, 256, 167.06, 167.01, 167.03, 604/164.02, 167.02, 167.04, 506, 513, 158, 604/164.01
See application file for complete search history.

(56) References Cited

U.S. PATENT DOCUMENTS

| 4,007,909 A | 2/1977 | Buseth et al. |
| 4,126,133 A | 11/1978 | Schwartz |
| 4,473,211 A | 9/1984 | Fremy |
| 4,586,694 A | 5/1986 | Jones |
| 4,655,752 A * | 4/1987 | Honkanen et al. ............ 604/256 |
| 4,665,752 A | 5/1987 | Huschelrath et al. |
| 4,686,977 A | 8/1987 | Cosma |
| 4,874,378 A | 10/1989 | Hillstead |
| 4,917,668 A | 4/1990 | Haindl |

(Continued)

FOREIGN PATENT DOCUMENTS

| EP | 0696459 A | 2/1996 |
| EP | 1671596 A | 6/2006 |
| WO | WO2006/020267 A | 2/2006 |

OTHER PUBLICATIONS

European Search Report for corresponding EP 07252539 date of mailing is Oct. 2, 2008 (3 pages).

*Primary Examiner* — Kevin C Sirmons
*Assistant Examiner* — Shefali Patel (57) ABSTRACT

A surgical seal assembly, includes a seal housing defining a longitudinal housing axis and having a longitudinal opening therethrough, a seal having an inner seal portion defining a passage and being adapted to form a substantial seal about a surgical instrument disposed within the passage and a guide mounted to the seal housing. The guide has an inner guide portion proximal of the inner seal portion of the seal and spaced therefrom. The inner guide portion defines a channel adapted to generally direct the surgical instrument toward the inner seal portion of the seal upon entry of the surgical instrument within the longitudinal opening of the seal housing. The inner guide portion is relatively compliant to accommodate initial offset or angled entry of the surgical instrument.

27 Claims, 5 Drawing Sheets

(56) References Cited

U.S. PATENT DOCUMENTS

| | | | |
|---|---|---|---|
| 4,929,235 A | 5/1990 | Merry et al. | |
| 4,960,412 A | 10/1990 | Fink | |
| 5,123,634 A | 6/1992 | Schwerdt | |
| 5,127,626 A | 7/1992 | Hilal et al. | |
| 5,195,980 A * | 3/1993 | Catlin | 604/167.04 |
| 5,197,955 A | 3/1993 | Stephens et al. | |
| 5,201,714 A | 4/1993 | Gentelia et al. | |
| 5,209,736 A | 5/1993 | Stephens et al. | |
| 5,209,737 A | 5/1993 | Ritchart et al. | |
| 5,211,633 A | 5/1993 | Stouder, Jr. | |
| 5,221,264 A | 6/1993 | Wilk et al. | |
| 5,224,930 A | 7/1993 | Spaeth et al. | |
| 5,242,412 A | 9/1993 | Blake, III | |
| 5,251,873 A | 10/1993 | Atkinson et al. | |
| 5,273,545 A | 12/1993 | Hunt et al. | |
| 5,295,657 A | 3/1994 | Atkinson | |
| 5,300,033 A | 4/1994 | Miller | |
| 5,300,035 A | 4/1994 | Clement | |
| 5,308,336 A | 5/1994 | Hart et al. | |
| 5,330,436 A | 7/1994 | Heidmueller | |
| 5,338,307 A | 8/1994 | Stephens et al. | |
| 5,342,315 A | 8/1994 | Rowe et al. | |
| 5,476,475 A | 12/1995 | Gadberry | |
| 5,478,318 A | 12/1995 | Yoon | |
| 5,492,304 A | 2/1996 | Smith et al. | |
| 5,496,280 A | 3/1996 | Vandenbroek et al. | |
| 5,509,643 A | 4/1996 | Carstens et al. | |
| 5,512,053 A | 4/1996 | Pearson et al. | |
| 5,514,133 A | 5/1996 | Golub et al. | |
| 5,531,758 A | 7/1996 | Uschold et al. | |
| 5,540,661 A | 7/1996 | Tomisaka et al. | |
| 5,545,142 A | 8/1996 | Stephens et al. | |
| 5,554,124 A | 9/1996 | Alvarado | |
| 5,569,205 A | 10/1996 | Hart et al. | |
| 5,569,206 A | 10/1996 | Gorman, Jr. et al. | |
| 5,584,850 A | 12/1996 | Hart et al. | |
| 5,603,702 A * | 2/1997 | Smith et al. | 604/256 |
| 5,607,397 A | 3/1997 | Stephens et al. | |
| 5,613,663 A | 3/1997 | Schmidt et al. | |
| 5,628,732 A | 5/1997 | Antoon, Jr. et al. | |
| 5,634,908 A | 6/1997 | Loomas | |
| 5,657,963 A * | 8/1997 | Hinchliffe et al. | 251/149.1 |
| 5,662,615 A | 9/1997 | Blake, III | |
| 5,676,657 A | 10/1997 | Yoon | |
| 5,709,664 A | 1/1998 | Vandenbroek et al. | |
| 5,720,759 A | 2/1998 | Green et al. | |
| 5,752,938 A | 5/1998 | Flatland et al. | |
| 5,755,702 A | 5/1998 | Hillstead et al. | |
| 5,779,697 A | 7/1998 | Glowa et al. | |
| 5,782,817 A | 7/1998 | Franzel et al. | |
| 5,792,113 A | 8/1998 | Kramer et al. | |
| 5,807,338 A | 9/1998 | Smith | |
| 5,820,600 A | 10/1998 | Carlson et al. | |
| 5,820,604 A | 10/1998 | Fox et al. | |
| 5,820,606 A | 10/1998 | Davis et al. | |
| 5,827,228 A | 10/1998 | Rowe | |
| 5,865,817 A | 2/1999 | Moenning et al. | |
| 5,868,714 A | 2/1999 | Danks | |
| 5,871,471 A | 2/1999 | Ryan et al. | |
| 5,879,368 A | 3/1999 | Hoskin et al. | |
| 5,895,377 A | 4/1999 | Smith et al. | |
| 5,906,595 A | 5/1999 | Powell et al. | |
| 5,989,224 A | 11/1999 | Exline et al. | |
| 5,993,471 A | 11/1999 | Riza et al. | |
| 6,000,670 A | 12/1999 | Okamoto | |
| 6,024,729 A * | 2/2000 | Dehdashtian et al. | 604/256 |
| 6,030,403 A | 2/2000 | Long et al. | |
| RE36,702 E | 5/2000 | Green et al. | |
| 6,066,117 A | 5/2000 | Fox et al. | |
| 6,068,011 A | 5/2000 | Paradis | |
| 6,077,249 A | 6/2000 | Dittrich et al. | |
| 6,077,288 A | 6/2000 | Shimomura et al. | |
| 6,083,203 A | 7/2000 | Yoon | |
| 6,093,176 A | 7/2000 | Dennis | |
| 6,110,154 A | 8/2000 | Shimomura et al. | |
| 6,123,689 A | 9/2000 | To et al. | |
| 6,159,182 A | 12/2000 | Davis et al. | |
| 6,176,843 B1 | 1/2001 | DiCaprio et al. | |
| 6,197,002 B1 | 3/2001 | Peterson | |
| 6,217,555 B1 | 4/2001 | Hart et al. | |
| 6,287,280 B1 * | 9/2001 | Lampropoulos et al. | 604/167.03 |
| D449,887 S | 10/2001 | Haberland et al. | |
| 6,482,181 B1 | 11/2002 | Racenet et al. | |
| 6,551,282 B1 | 4/2003 | Exline et al. | |
| 6,595,946 B1 | 7/2003 | Pasqualucci | |
| 6,702,787 B2 * | 3/2004 | Racenet et al. | 604/256 |
| 2003/0195472 A1 | 10/2003 | Green et al. | |
| 2004/0171990 A1 * | 9/2004 | Dennis et al. | 604/167.03 |

\* cited by examiner

SURGICAL SEAL ASSEMBLY

CROSS-REFERENCE TO RELATED APPLICATIONS

The present application claims the benefit of and priority to U.S. Provisional Application Ser. No. 60/819,434 filed on Jul. 7, 2006.

BACKGROUND

1. Technical Field

The present disclosure relates to a surgical device and, more particularly, relates to a surgical seal assembly for a cannula assembly and having a compliant guide for directing a surgical instrument along a path generally coincident with a seal axis.

2. Description of the Prior Art

Minimally invasive surgical procedures including both endoscopic and laparoscopic procedures permit surgery to be performed on organs, tissues and vessels far removed from an opening within the tissue. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. These procedures typically employ surgical instruments which are introduced into the body through a cannula. The cannula has a housing at a proximal end thereof in which a seal assembly is mounted. The seal assembly provides a substantially fluid tight seal about the instrument to preserve the integrity of the established pneumoperitoneum.

Minimally invasive procedures have several advantages over traditional open surgery, including less patient trauma, reduced recovery time, reduced potential for infection, etc . . . However, despite its recent success and overall acceptance as a preferred surgical technique, minimally invasive surgery, such as laparoscopy, has several disadvantages. In particular, the insertion of the surgical instrument within the cannula has proven to be difficult in certain procedures, e.g., in procedures requiring extensive manipulation of the long narrow endoscopic instruments within a remote site. In addition, many conventional seal assemblies are not particularly well-adapted to receive a surgical instrument if it is inserted at an angle. This type of insertion often results in the instrument missing the target (e.g. septum seal, etc.) and becoming lodged in an undesirable location within the seal assembly. There remains a need for an apparatus that may be used to guide a surgical instrument through a seal assembly in a more efficient and efficacious manner.

SUMMARY

Accordingly, a surgical seal assembly for use with a cannula assembly is disclosed. The surgical seal assembly includes a seal housing defining a longitudinal housing axis and having a longitudinal opening therethrough, a seal having an inner seal portion defining a passage and being adapted to form a substantial seal about a surgical instrument disposed within the passage and a guide mounted to the proximal end of the seal housing. The guide has an inner guide portion proximal of the inner seal portion of the seal and spaced therefrom. The inner guide portion defines a channel adapted to generally direct the surgical instrument toward the inner seal portion of the seal upon entry of the surgical instrument within the longitudinal opening of the seal housing. The inner guide portion is relatively compliant to accommodate initial offset or angled entry of the surgical instrument. The inner guide portion of the guide may include an elastomeric material.

The channel of the guide is generally tapered in configuration, having a proximal entry opening and a distal exit opening. The distal exit opening defines an internal dimension less than a corresponding internal dimension of the proximal exit opening. The channel may define a general frusto-conical configuration. The inner guide portion of the guide is adapted to permit passage of the surgical instrument through the channel without forming a seal about the surgical instrument. The guide may include a plurality of compliant members. The compliant members preferably extend at least radially inwardly relative to the longitudinal axis. Preferably, the compliant members extend in a general direction having radial and longitudinal components of direction relative to the longitudinal axis. The compliant members may be mounted in cantilevered relation to the seal housing and may pivot slightly upon engagement with the surgical instrument. The compliant members may be arranged such that adjacent compliant members are in partial overlapping relation.

The seal housing includes an internal wall defining an internal dimension less than the internal dimension of the proximal entry opening of the channel of the guide to generally restrict the internal dimension of the longitudinal opening of the seal housing.

In another embodiment, a surgical assembly includes a cannula assembly and a seal assembly. The cannula assembly includes a cannula housing and a cannula sleeve extending from the cannula housing. The cannula provides access to an underlying surgical site. The seal assembly includes a seal housing adapted for releasable connection to the cannula housing and having a longitudinal opening therethrough, a seal having inner seal portions adapted to form a substantial seal about a surgical instrument and a guide connected to an exterior surface of the seal housing. The guide includes a relatively compliant inner guide portion adapted to accommodate initial offset entry of the surgical instrument within the seal housing and being mounted with respect to the seal housing to direct the surgical instrument toward the inner seal portion of the seal during continued advancement of the instrument through the longitudinal opening of the seal housing. The cannula assembly may include a valve adapted to close in the absence of the surgical instrument inserted therethrough and open in the presence of the surgical instrument. The inner guide portion of the guide is isolated from the inner seal portion of the seal to not interfere with the functioning of the seal. The guide may include a plurality of compliant members coaxially arranged about the longitudinal axis. The inner guide portion of the guide is adapted to permit passage of the surgical instrument through the channel without forming a seal about the surgical instrument. The guide may be disposed proximal of the seal.

A method for performing a surgical procedure is also disclosed. The method includes the steps of:

accessing an underlying operative site with a cannula assembly;

mounting a seal assembly to the cannula assembly, the seal assembly including a seal housing, a seal mounted within the seal housing and a guide mounted to the seal housing proximal of the seal;

introducing a surgical instrument within the seal assembly whereby the guide generally directs the surgical instrument toward an internal passage of the seal without forming a seal thereabout, the guide being spaced from the internal passage so as to not interfere with the functioning of the seal; and performing a surgical procedure with the surgical instrument

BRIEF DESCRIPTION OF THE DRAWINGS

Preferred embodiments of the present disclosure are described hereinbelow with references to the drawings, wherein.

DETAILED DESCRIPTION OF THE PREFERRED EMBODIMENT(S)

The surgical seal assembly of the present disclosure provides a substantial seal between a body cavity of a patient and the outside atmosphere during insertion of a surgical instrument through the assembly. Moreover, the seal assembly guides the instrument through the assembly and places it in a desirable position for passage through the seal. This guide greatly facilitates endoscopic surgery where surgical instruments may be introduced off-axis or angulated with respect to the seal axis and as a result could become lodged within the seal assembly. The surgical seal assembly may be adapted for mounting to a conventional cannula assembly as will be described hereinbelow.

The presently disclosed seal assembly contemplates the introduction of various types of surgical instruments adapted for insertion through an elongated trocar assembly. Some possible examples of such instruments may include clip appliers, graspers, dissectors, retractors, staplers, laser fibers, photographic devices, endoscopes and laparoscopes, tubes etc. Such instruments are collectively referred to herein as instruments.

In the following description, the term "proximal" refers to the portion of the instrument closest to the operator, while the term "distal" refers to the portion of the instrument remote from the operator.

Figure 1:
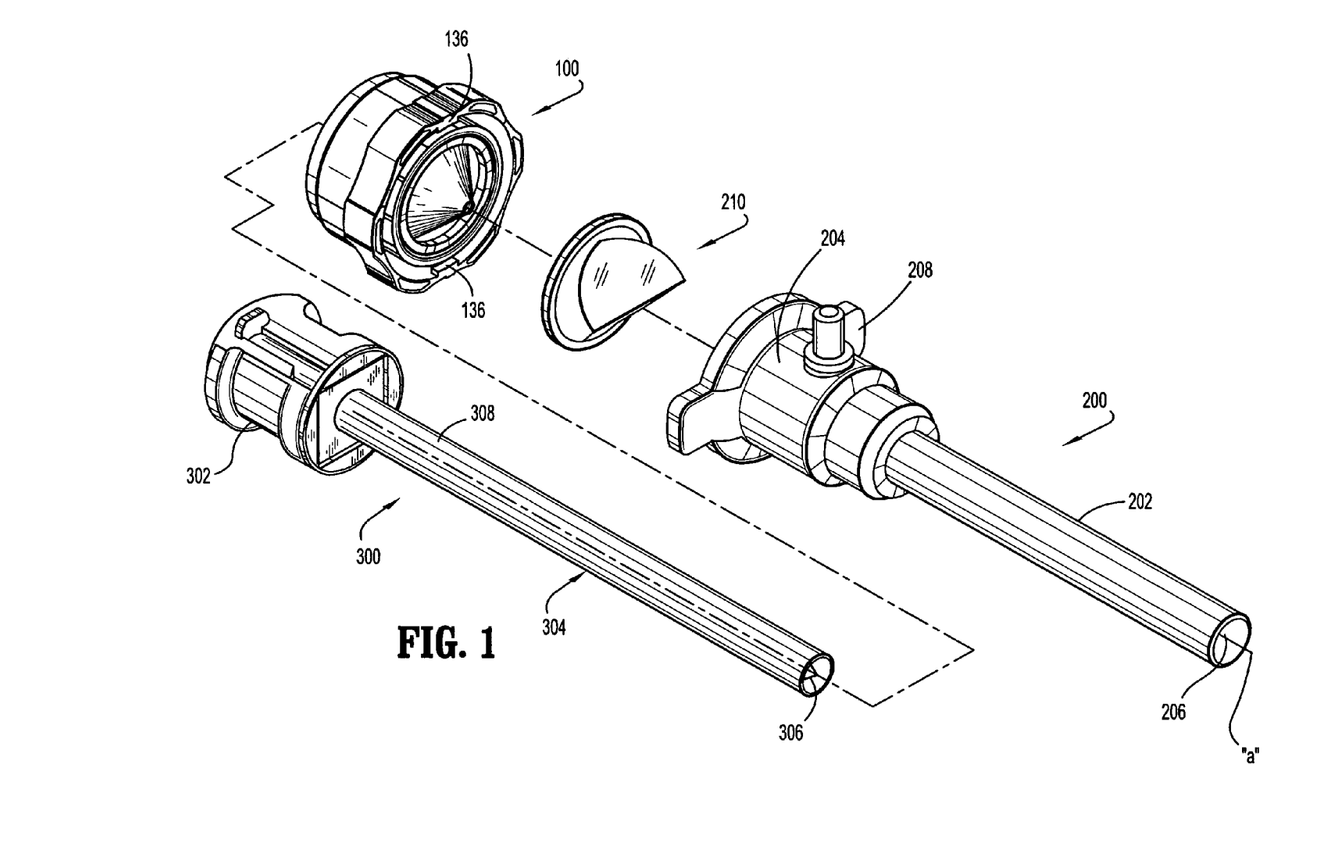
FIG. 1 is a perspective view with parts separated of the seal assembly of the present disclosure in accordance with the principles of the present disclosure illustrated with a cannula assembly and a trocar assembly.

Referring to FIG. 1, the seal assembly 100 of the present disclosure is shown with a cannula assembly 200. Cannula assembly 200 may be any conventional cannula assembly suitable for the intended purpose of accessing a body cavity and permitting introduction of instruments therethrough. Cannula assembly 200 is particularly adapted for use in laparoscopic surgery where the peritoneal cavity is insufflated with a suitable gas, e.g., $CO_2$, to raise the cavity wall from the internal organs therein. The cannula assembly 200 is typically used with an obturator assembly 300 which is an elongate instrument positionable within the cannula assembly. The obturator assembly 300 may have a sharp end or a blunt end and is utilized to pass through, e.g., abdominal tissue, to facilitate introduction of the cannula assembly within the abdominal cavity. Once access to the abdominal cavity is achieved, the obturator assembly 300 is removed from the cannula assembly 200 leaving the cannula assembly 200 in place for introduction of the surgical instrumentation utilized to perform the procedure. Examples of cannula assemblies in which the present seal assembly 100 may be utilized are disclosed in commonly assigned U.S. Pat. No. 5,603,702 to Smith et al., which issued on Feb. 18, 1997, and commonly assigned U.S. Pat. No. 5,807,338 to Smith et al., which issued on Sep. 15, 1998, the entire contents of each disclosure being hereby incorporated by reference herein.

Cannula assembly 200 includes cannula sleeve 202 and cannula housing 204 mounted to an end of the sleeve 202. Cannula sleeve 202 defines a longitudinal axis "a" extending along the length of sleeve 202. Sleeve 202 further defines an internal longitudinal passage 206 dimensioned to permit passage of surgical instrumentation.

Cannula housing 204 may be a multi-component element secured via a snap fit, ultrasonic welding or any other means envisioned by one skilled in the art including, e.g., adhesive means. Cannula housing 204 may further include diametrically opposed housing grips 208 dimensioned and arranged for gripping engagement by the fingers of the user. Cannula housing 204 may further include an internal duck bill or zero closure valve 210. Such zero closure valve 210 opens to permit passage of the surgical instrumentation and closes in the absence of the instrumentation. The valve may be preferably adapted to close upon exposure to the forces exerted by the insufflation gases in the internal cavity. Other zero closure valves are also contemplated including single or multiple slit valve arrangements, trumpet valves, flapper valves, etc.

Cannula sleeve 202 and cannula housing 204 may be formed of stainless steel or other rigid materials such as a polymeric material or the like. Cannula sleeve 202 and/or cannula housing 204 may be clear or opaque. The diameter of sleeve 202 may vary, but typically ranges from 10 to 15 mm for use with the seal assembly 100 of the present disclosure.

Obturator assembly 300 includes obturator housing 302 and obturator member 304 extending from the housing 302. Obturator member 304 includes a penetrating end 306 adjacent its distal end. Penetrating end 306 may be sharp or blunt. An obturator sleeve 308 is coaxially mounted about obturator member 304. Obturator sleeve 308 may retract to expose piercing end 306. Alternatively, obturator member 304 may be advanced within obturator sleeve 308 to expose piercing end 306. Other alternate obturator mechanisms for exposing penetrating end 306 are also envisioned.

Figure 2:
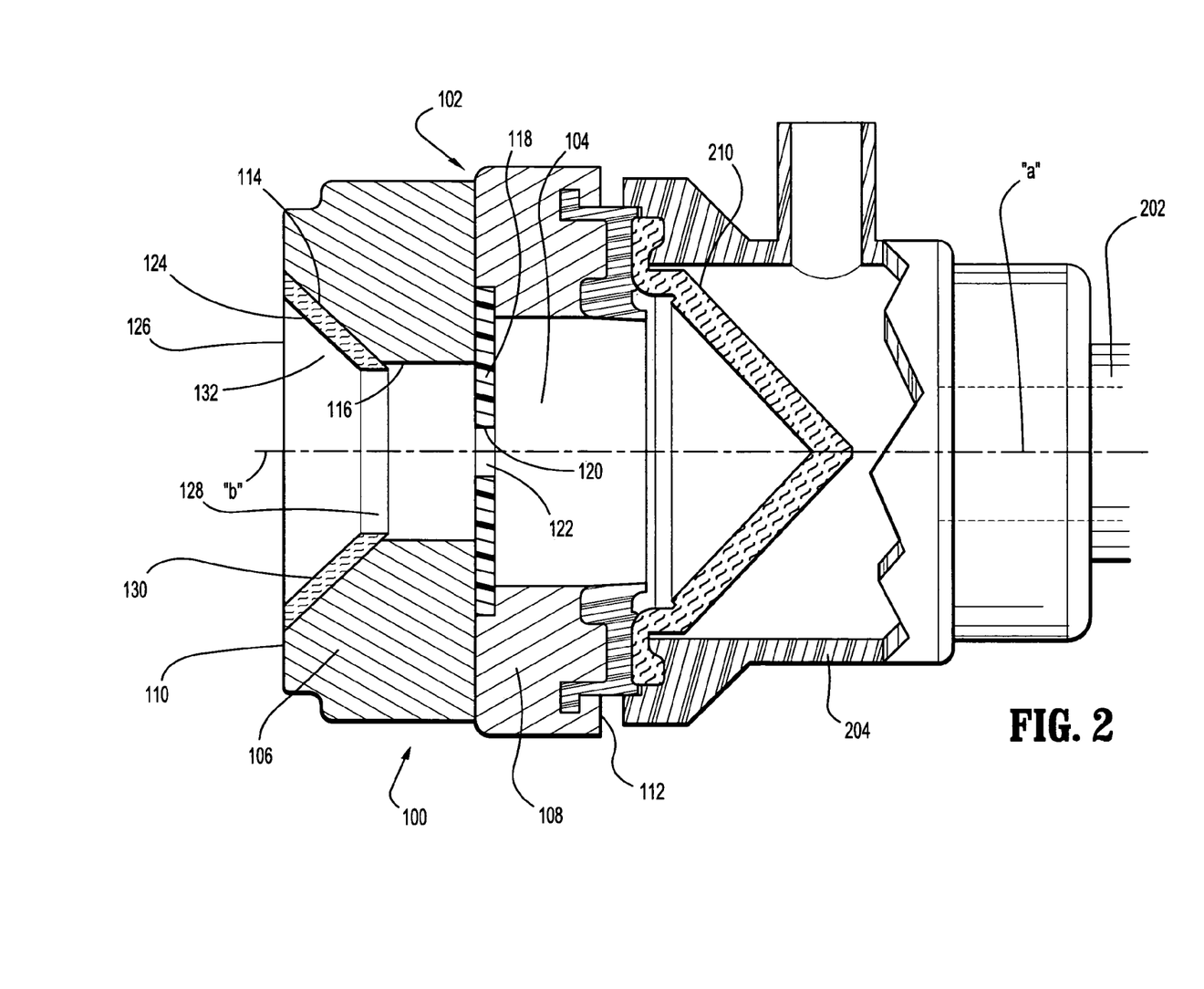
FIG. 2 is a side cross-sectional view of the surgical seal assembly of FIG. 1.

Referring now to FIG. 2, in conjunction with FIG. 1, seal assembly 100 will be discussed in detail. Seal assembly 100 includes seal housing, generally identified as reference numeral 102, and longitudinal opening 104 extending through seal housing 102. Seal housing 102 houses the sealing components of the assembly and defines central seal housing axis "b" which is preferably parallel to the axis "a" of cannula sleeve 202 and, more preferably, coincident with the axis "a" of the cannula when the seal assembly 100 is mounted to the cannula assembly 200. In one embodiment, seal housing 102 may incorporate several housing components 106, 108 which, when assembled together, form the seal housing 102. Assembly of housing components 106, 108 may be effected by any suitable adhesive means including adhesives, cements or the like or mechanical means including tongue groove arrangements, bayonet couplings, interference fits, etc. Alternatively, seal housing 102 may be monolithically formed as a single unit.

Seal housing 102 defines proximal and distal ends 110, 112, respectively. Adjacent proximal end 110 is internal tapered wall 114 which extends radially inwardly toward seal housing axis "b" from proximal to distal, i.e., tapered wall 114 has both longitudinal and radial components of direction, and terminates in internal annular wall 116. Annular wall 116 serves to restrict the internal dimension of longitudinal opening 104 to at least partially constrain lateral movement of a surgical instrument introduced through seal housing 102.

Seal housing 102 may be constructed of a plurality of different materials, including, but not limited to, polymeric, metallic, or elastomeric. Preferably, the components of seal housing 102 are formed of a polycarbonate material such as ABS available from the General Electric Company. Seal housing 102 may further include a handle which may be of any suitable ergonomic design. Moreover, seal housing 102 may be used in conjunction with, or detachably mounted, to cannula assembly 200 such as those described hereinabove.

Seal assembly 100 includes seal 118 mounted within seal housing 102 in suspended relation. Seal 118 may be mounted within seal housing 102 through conventional means such as for example with the use of adhesives, cements or the like. Alternatively, or in conjunction with the aforementioned adhesive means, seal 118 may be disposed or trapped between housing components 106,108 of seal housing 102 to effect the mounting. It is also envisioned that seal 118 may be mounted in a manner which permits radial or lateral movement of the seal 118 within seal housing 102.

Seal 118 preferably includes inner seal portion 120 defining a passage adapted to form a substantial seal about a surgical instrument. Seal 118 may be a septum seal incorporating a circular aperture 122 formed of any suitable elastomeric material. In one embodiment, seal 118 is the fabric seal disclosed in commonly assigned U.S. Pat. No. 6,702,787 to Racenet et al., the entire contents of which are incorporated herein by reference. The seal disclosed in the '787 patent may be a flat septum seal having a first layer of resilient material and a second fabric layer juxtaposed relative to the first layer. The fabric layer may include a SPANDEX material containing 20% LYCRA from Milliken. In yet another alternative, seal 118 is preferably a fabric seal and is desirably arranged so as to have a constriction. The fabric is desirably constructed of a material that forms a constriction or closure. The seal may also be molded with a resilient material so as to have a constriction. Other arrangements for seal 118 are also envisioned.

Although seal 118 is disclosed as an impregnated fabric arrangement, it is appreciated that other seal types may be used and still achieve the objectives of the present disclosure. For example, seal 118 may be fabricated from an elastomeric material without the embedded fabric. Gel, foams, or other fluid-filled bladder seal arrangements are also envisioned.

Figure 3:
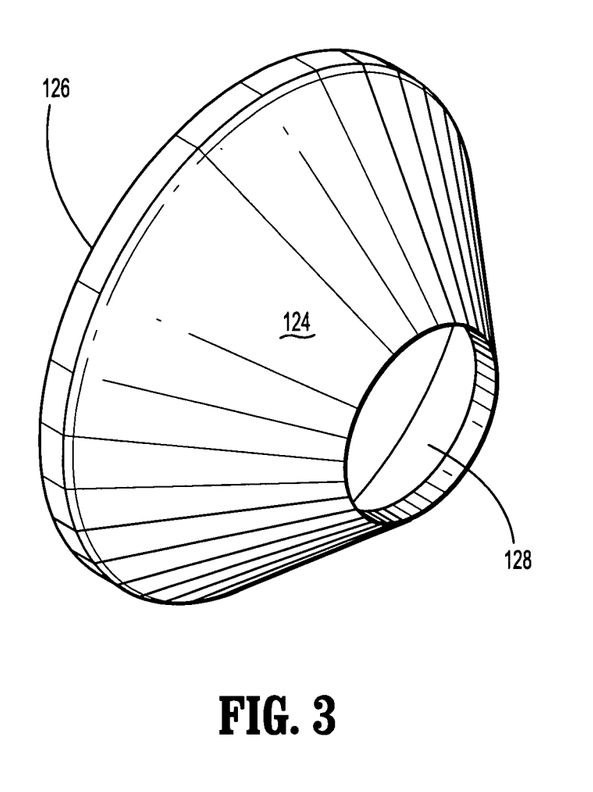
FIG. 3 is a perspective view of the compliant guide of the surgical seal assembly of FIGS. 1-2.

Referring now to FIGS. 2-3, seal assembly 100 further includes generally compliant guide 124 which is mounted to an exterior surface of seal housing 102 preferably adjacent internal tapered wall 114. Compliant guide 124 may be secured to the exterior surface, e.g., internal tapered wall 114 of seal housing 102 or mounted in suspended relation to the internal tapered wall 114. Compliant guide 124 is generally tapered in configuration, e.g., generally frusto-conical shaped, having proximal entry opening 126 and distal exit opening 128, and inner guide portion 130 defining internal channel 132. Preferably, distal exit opening 128 defines an internal dimension greater than a corresponding internal dimension of aperture 122 of seal 118. In a preferred embodiment, inner guide portion 130 is dimensioned to permit passage of the surgical instrument through internal channel 132 without forming a seal about the surgical instrument.

In use, compliant guide 124 is adapted to generally direct the instrument toward the inner seal portion 120 of seal 118 upon advancement of the instrument through longitudinal opening 104 of seal housing 102. In one preferred embodiment, compliant guide 124 has a compliant characteristic which permits the compliant guide 124 to deflect upon engagement by a surgical instrument, such as, e.g., when an instrument is initially introduced off axis or angulated with respect to the seal housing axis "b", to substantially prevent lodging of the instrument within the compliant guide 124. Thereafter, the tapered orientation of compliant guide 124 guides the instrument along the seal axis "b". Compliant guide 124 may be constructed of a number of different compliant or flexible materials. In a preferred embodiment, compliant guide 124 is formed of an elastomeric material. Compliant guide 124 is preferably longitudinally spaced from seal 118 so as to not interfere with the functioning of the seal 118.

It is envisioned that seal assembly 100 may be detachably connected to cannula assembly 200. Preferably, seal housing 102 is dimensioned to be releasably mounted to cannula housing 204. In this regard, it is appreciated that seal housing 102 and cannula housing 204 may incorporate means for facilitating the releasable connection of seal assembly 100 to cannula assembly 200 including, e.g., an interference fit, bayonet coupling, screw arrangement, etc . . . on corresponding structure of the seal housing 102 and cannula housing 204. For example, seal housing 102 may include locking detents 136 (FIG. 1) which engage corresponding structure on cannula housing 204 to secure seal assembly 100 to cannula assembly 200. One suitable means for connecting the seal and cannula assemblies 100, 200 is disclosed in the aforementioned U.S. Pat. No. 5,603,702 to Smith et al. Thus, the surgeon can remove seal assembly 100 from the cannula assembly 200 at any time during the surgical procedure and similarly, mount the seal assembly 100 to the cannula when desired in order to provide a sealing engagement with an instrument to be inserted through the cannula. In addition, seal assembly 100 may be readily adapted for mounting to conventional cannula of differing structures. Alternatively, seal housing 102 may be permanently secured to cannula housing 204 if desired.

Figure 4:
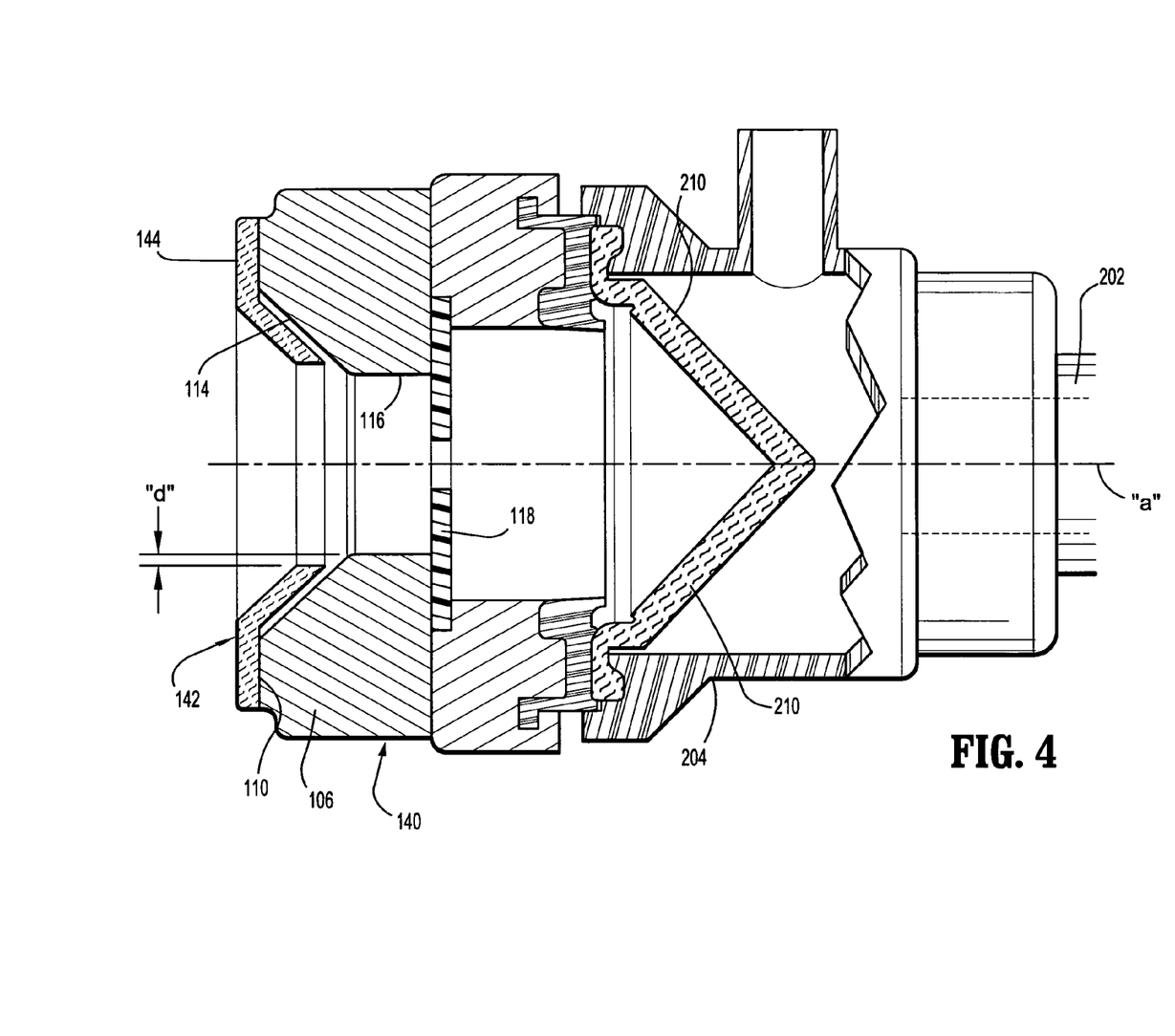
FIG. 4 is a side cross-sectional view of an alternate embodiment of the surgical seal assembly of the present disclosure.

Referring now to FIG. 4, another embodiment of the seal assembly of the present disclosure will be discussed. Seal assembly 140 is substantially similar to seal assembly 100 discussed hereinabove. However, in accordance with this embodiment, seal assembly 140 includes compliant guide 142. Compliant guide 142 is mounted in cantilever manner to seal housing 106 to provide a greater degree of flexing capability to the compliant guide 142. In this regard, compliant guide 142 is spaced from internal tapered wall 114. In addition, the effective internal dimension adjacent the distal end of compliant guide 142 is less than the internal dimension or diameter of annular wall 116, i.e., compliant guide 142 is spaced a distance "d" from annular wall 116 such that the compliant guide 142 does not necessarily restrict the diameter of the opening of housing component 106. Any means for mounting compliant guide 142 in a pivotal manner may be appreciated by one skilled in the art. In one preferred embodiment, compliant guide 142 includes flange 144 which is affixed through conventional means to proximal exterior surface 110 of housing component 106. In other respects, seal assembly 140 operates in a similar manner to that described hereinabove.

Figure 5:
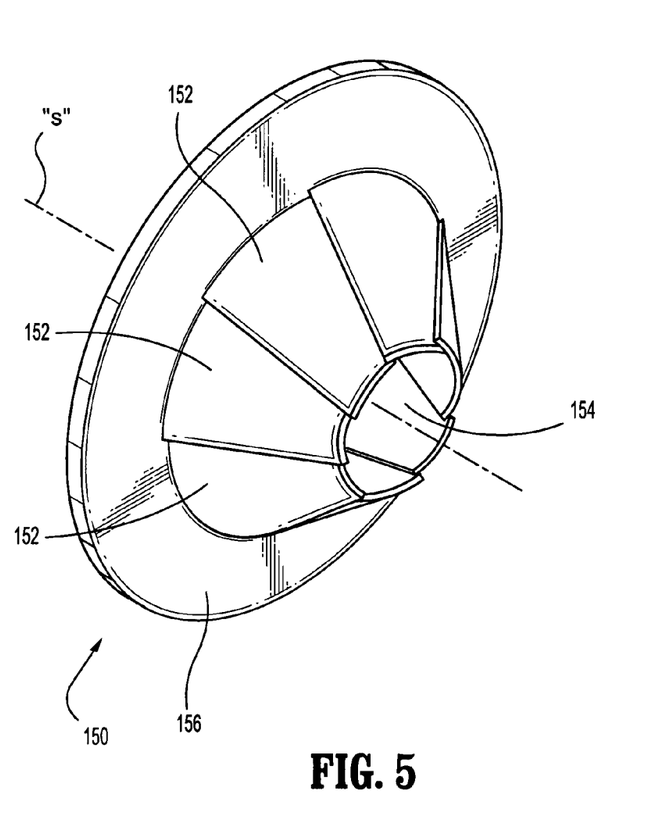
FIG. 5 is a perspective view of a compliant guide having a plurality of compliant members in accordance with another alternate embodiment of the surgical seal assembly.

FIG. 5 illustrates an alternate embodiment of a compliant guide for incorporation with the seal assembly of the present disclosure. Compliant guide 150 includes a plurality of compliant members 152 coaxially arranged about seal axis "s" to define opening 154. Compliant guide 150 may be mounted to seal housing 106 in pivotal relation substantially in the same manner as discussed in connection with the embodiment of FIG. 4 so as to provide a greater degree of flexibility upon engagement and initial entry of the surgical instrument. In this regard, compliant guide 150 includes flange 156 which is secured to proximal surface 110 of housing component 106 (see FIG. 4). Compliant members 152 may be spaced from internal tapered wall 114 in suspended pivotal manner to provide a greater degree of deflection upon offset entry of the surgical instrument. Compliant members 152 are arranged to define a general frusto-conical shape extending radially inwardly relative to the seal axis "s" from proximal to distal, and may be further arranged such that adjacent compliant members 152 are in overlapping or partial overlapping relation with each other. Compliant members 152 are flexible to deflect, bend, etc. upon engagement with the inserted surgical object and are preferably fabricated from on elastomeric material. Any shape, including, but not limited to, rectangular, rounded, triangular, etc. are envisioned for complaint members 152.

It will be understood that various modifications and changes in form and detail may be made to the embodiments of the present disclosure without departing from the spirit and scope of the invention. Therefore, the above description should not be construed as limiting the invention but merely as exemplifications of preferred embodiments thereof. Those skilled in the art will envision other modifications within the scope and spirit of the present invention as defined by the claims appended hereto. Having thus described the invention with the details and particularity required by the patent laws, what is claimed and desired protected is set forth in the appended claims.

What is claimed is:

1. A surgical seal assembly, which comprises:
 a seal housing defining a longitudinal axis and having a longitudinal opening therethrough, the seal housing defining proximal and distal ends;
 a seal having an inner seal portion defining a passage and being adapted to form a seal about a surgical instrument disposed within the passage; and
 a guide mounted adjacent an internal tapered wall of the seal housing and longitudinally fixed relative to the seal, at least a portion of the guide is longitudinally aligned with and disposed radially inward of the internal tapered wall of the seal housing, the guide having an inner guide portion proximal of the inner seal portion of the seal and spaced therefrom, the inner guide portion positioned and arranged to not contact the inner seal portion during insertion of the surgical instrument through the passage of the seal, the inner guide portion defining a channel adapted to direct the surgical instrument toward the inner seal portion of the seal upon entry of the surgical instrument within the longitudinal opening of the seal housing, the inner guide portion being compliant to accommodate initial offset or angled entry of the surgical instrument, the inner guide portion of the guide being dimensioned and adapted to permit passage of the surgical instrument through the channel without forming a seal about the surgical instrument.

2. The surgical seal assembly according to claim 1 wherein the inner guide portion of the guide includes an elastomeric material.

3. The surgical seal assembly according to claim 1 wherein the channel of the inner guide portion is tapered in configuration, having a proximal entry opening and a distal exit opening, the distal exit opening defining an internal dimension less than a corresponding internal dimension of the proximal entry opening.

4. The surgical seal assembly according to claim 1 wherein the channel defines a frusto-conical configuration.

5. The surgical seal assembly according to claim 1 wherein the guide includes a plurality of compliant members, the compliant members extending at least radially inwardly relative to the longitudinal axis.

6. The surgical seal assembly according to claim 5 wherein the compliant members are mounted in cantilevered relation to the seal housing.

7. The surgical seal assembly according to claim 5 wherein the compliant members are arranged such that adjacent compliant members at least partially overlap each other.

8. The surgical seal assembly according to claim 5 wherein the compliant members extend in a direction having radial and longitudinal components of direction relative to the longitudinal axis.

9. The surgical seal assembly according to claim 1 wherein the seal housing includes an internal wall defining an internal dimension less than an internal dimension of a proximal entry opening of the channel of the inner guide portion to restrict an internal dimension of the longitudinal opening of the seal housing.

10. The surgical seal assembly of claim 1 further comprising a zero closure valve.

11. The surgical seal assembly of claim 1 wherein the seal housing defines a channel including a tapered section, and wherein the guide is spaced from the tapered section along the longitudinal axis.

12. The surgical seal assembly of claim 1 wherein the guide defines surfaces extending along axes intersecting the longitudinal axis.

13. The surgical seal assembly of claim 1 wherein the passage defined by the seal includes a proximal opening defining an internal dimension, and the channel defined by the inner guide portion is tapered in configuration and includes proximal and distal openings, the proximal opening of the channel defined by the inner guide portion being larger than the distal opening of the channel defined by the inner guide portion, and the distal opening of the channel defined by the inner guide portion being larger than the internal dimension of the proximal opening of the passage defined by the seal.

14. The surgical seal assembly of claim 1 wherein the guide is spaced from the seal along the longitudinal axis in a manner preventing interference with functioning of the seal.

15. The surgical seal assembly according to claim 1, wherein the guide is suspended from the internal tapered wall of the seal housing.

16. The surgical seal assembly according to claim 1, wherein the internal tapered wall of the seal housing is positioned and arranged to be prevented from contacting the surgical instrument during insertion of the surgical instrument.

17. A surgical assembly, which comprises:
 a cannula assembly including a cannula housing and a cannula sleeve extending from the cannula housing, the cannula assembly providing access to an underlying surgical site; and
 a seal assembly, the seal assembly including:
  a seal housing adapted for releasable connection to the cannula housing, the seal housing defining a longitudinal axis and having a longitudinal opening therethrough;
  a seal having an inner seal portion adapted to form a seal about a surgical instrument; and
  a guide mounted to an internal tapered wall of the seal housing and longitudinally fixed relative to the seal, the guide including a compliant inner guide portion adapted to accommodate initial offset entry of the surgical instrument within the seal housing and being mounted with respect to the seal housing to direct the surgical instrument toward the inner seal portion of the seal during continued advancement of the surgical instrument through the longitudinal opening of the seal housing, the inner guide portion of the guide being spaced from the inner seal portion in non-contacting relation therewith, the inner guide portion of the guide being dimensioned and adapted to permit passage of the surgical instrument through a channel defined therein without forming a seal about the surgical instrument.

18. The surgical assembly according to claim 17 wherein the cannula assembly includes a valve adapted to close in an absence of the surgical instrument inserted therethrough and open in a presence of the surgical instrument.

19. The surgical assembly according to claim 17 wherein the inner guide portion of the guide is isolated from the inner seal portion of the seal to not interfere with functioning of the seal.

20. The surgical assembly according to claim 19 wherein the guide includes a plurality of compliant members coaxially arranged about the longitudinal axis.

21. The surgical assembly according to claim 17 wherein the guide is disposed proximal of the seal.

22. The surgical assembly of claim 17 further comprising a zero closure valve.

23. The surgical assembly of claim 17 wherein the channel is tapered in configuration and has a proximal entry opening and a distal exit opening, the distal exit opening defining an internal dimension less than a corresponding internal dimension of the proximal entry opening.

24. The surgical assembly of claim 17 wherein the guide is spaced from the seal along the longitudinal axis in a manner preventing interference with functioning of the seal.

25. A method for performing a surgical procedure, comprising:

accessing an underlying operative site with a cannula assembly, the operative site being insufflated with insufflation fluids;

mounting a seal assembly to the cannula assembly, the seal assembly including a seal housing defining a longitudinal axis, a seal mounted within the seal housing, and a guide mounted to an internal tapered wall of the seal housing proximal of the seal and longitudinally fixed relative to the seal, the guide comprising an inner guide portion defining a tapered orientation obliquely arranged relative to the longitudinal axis and having a compliant material;

introducing a surgical instrument within the seal assembly whereby the inner guide portion of the guide directs the surgical instrument toward an internal passage of the seal without the inner guide portion of the guide forming a seal thereabout, the guide being spaced from the internal passage so as to not interfere with functioning of the seal, and whereby the compliant material of the inner guide portion accommodates initial offset or angled entry of the surgical instrument and the seal establishes a seal about the surgical instrument; and performing the surgical procedure with the surgical instrument.

26. The method for performing a surgical procedure according to claim 17, wherein the step of introducing the surgical instrument includes passing the surgical instrument through a zero closure valve positioned within the seal housing in order to prevent escape of the insufflation fluids following withdrawal of the surgical instrument.

27. The method for performing a surgical procedure according to claim 25 wherein the step of mounting the seal assembly to the cannula assembly includes positioning the seal assembly such that the guide is spaced from the seal along the longitudinal axis so as to prevent interference with functioning of the seal.

* * * * *